United States Patent
Oonuki et al.

(10) Patent No.: US 8,216,149 B2
(45) Date of Patent: Jul. 10, 2012

(54) PUNCTURE ADAPTOR, ULTRASONIC PROBE FOR PUNCTURE, ULTRASONIC DIAGNOSTIC APPARATUS FOR PUNCTURE, METHOD FOR DETECTING ANGLE OF PUNCTURE NEEDLE

(75) Inventors: Yutaka Oonuki, Tochigi-ken (JP);
Hiroyuki Shikata, Tochigi-ken (JP);
Takashi Takeuchi, Tochigi-ken (JP)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 12/572,890

(22) Filed: Oct. 2, 2009

(65) Prior Publication Data
US 2010/0228131 A1 Sep. 9, 2010

Related U.S. Application Data

(63) Continuation of application No. 11/502,369, filed on Aug. 11, 2006, now abandoned.

(30) Foreign Application Priority Data
Aug. 11, 2005 (JP) .............................. P2005-233308

(51) Int. Cl.
*A61B 8/00* (2006.01)

(52) U.S. Cl. ....................................... 600/461; 600/464
(58) Field of Classification Search .................. 600/461, 600/464
See application file for complete search history.

(56) References Cited

U.S. PATENT DOCUMENTS

| | | | |
|---|---|---|---|
| 4,945,305 A | | 7/1990 | Blood |
| 5,647,373 A | * | 7/1997 | Paltieli .......................... 600/567 |
| 6,216,029 B1 | * | 4/2001 | Paltieli .......................... 600/427 |
| 6,695,786 B2 | * | 2/2004 | Wang et al. .................... 600/461 |

FOREIGN PATENT DOCUMENTS
JP 2004-305535 11/2004
* cited by examiner

*Primary Examiner* — Long V. Le
*Assistant Examiner* — Bradley Impink
(74) *Attorney, Agent, or Firm* — Oblon, Spivak, McClelland, Maier & Neustadt, L.L.P.

(57) ABSTRACT

An ultrasound diagnostic apparatus including an ultrasonic probe transmitting and receiving ultrasound toward and from a subject, a puncture adaptor configured to be fixed to the ultrasonic probe and to hold a puncture needle, wherein the puncture adaptor has moving part movable in relation to the ultrasonic probe with the puncture needle, and a sensor provided at the ultrasonic probe, and configured to detect the position of the moving part. As the puncture needle is moved relative to the probe, the movable part is correspondingly moved relative to the probe, and movement of the movable part, and therefore also of the puncture needle, is detected by the sensor.

15 Claims, 5 Drawing Sheets

PUNCTURE ADAPTOR, ULTRASONIC PROBE FOR PUNCTURE, ULTRASONIC DIAGNOSTIC APPARATUS FOR PUNCTURE, METHOD FOR DETECTING ANGLE OF PUNCTURE NEEDLE

CROSS REFERENCE TO RELATED APPLICATIONS

This application is a continuation of and claims the benefit of priority under 35 U.S.C. §120 from U.S. Ser. No. 11/502,369 filed Aug. 11, 2006, and claims the benefit of priority under 35 U.S.C. §119 from Japanese Patent Application No. 2005-233308 filed Aug. 11, 2005, the entire contents of each of which are incorporated herein by reference.

BACKGROUND OF THE INVENTION

An ultrasonic diagnostic apparatus is often used for puncture. In this case, an operator watches a monitor display of an ultrasound image of a live body and a puncture needle, and insertion of the puncture needle. In the puncture operation, a puncture adapter is often used, and a puncture guide marker is displayed on the monitor to serve as a direction guide to assist an operator during needle insertion. In one puncture method, a puncture adaptor is fixed at a predetermined position of an ultrasonic probe body. In this method, an operator must read an angle value by watching a scale on the adaptor, and set the angle value for displaying the angle of the puncture marker of the ultrasonic diagnostic apparatus. This setting enables display of the puncture guide image with an ultrasonic image on the display monitor. In this technique, which entails operator's reading and setting, an operator perform angle reading and setting every time the operator changes an angle of the puncture needle. This is complicated for the operator.

In another method, the above mentioned angle of the puncture needle guide is detected by a sensor set by the puncture guide, and the detected angle is delivered to a processing unit in an ultrasonic diagnostic apparatus. (For example, see JP2004-305535A.) The sensor detecting the angle of the puncture needle guide is provided near a part moving in accordance with the changing angle of the puncture needle, (for example, see FIG. 6 or FIG. 7 in JP2004-305535A) and the sensor detects the angle indirectly or directly. In this method, the puncture marker image displayed on the monitor is automatically changed in accordance with the detected angle.

However the puncture adaptor is often removably constructed so that operator can mount and remove it from a standard ultrasonic probe. In this case, provision must be made for delivering detected signal to the apparatus body. For example, in the case that probe cables double as the connection to apparatus body, a connection structure such as a connecter connecting to the ultrasonic probe and a cable leaded from the puncture adaptor is necessary. On the other hand, in the case that another cable is connected to the apparatus body, the increasing number of cables adversely impact operability, and providing a new connecter for puncture is needed.

Because a guiding portion of the puncture adaptor guides a needle inserted into a body, body fluid and body tissues adhere to the guides. In this situation, the guiding portion must be easily disinfected and sterilized or must be disposable. However, in the above mentioned case, use of the sensor makes the structure complicated, makes disinfection or sterilization of the guide difficult, and makes the guide too expensive to be disposable.

BRIEF SUMMARY OF THE INVENTION

According to one aspect of the present invention, there is provided an ultrasonic diagnostic apparatus, an ultrasonic probe, a puncture guide, and a method for detecting the angle of a puncture needle that does not require an operator to perform a bothersome operation for display of a puncture guide image.

According to another aspect of the present invention there is provided an ultrasound diagnostic apparatus including a ultrasonic probe configured to transmit and receive ultrasound toward and from a subject, puncture adaptor configured to be fixed at the ultrasonic probe and to hold a puncture needle, the puncture adaptor having moving part configured to move toward the ultrasonic probe with the puncture needle and a sensor provided at the ultrasonic probe and configured to detect a position of the moving part. The sensor can be one of an electromagnetic induction sensor, an electro-capacitance sensor, and an ultrasound sensor.

According to a further aspect of the present invention, there is provided an ultrasonic probe including a fixed puncture adaptor configured to hold a puncture needle, and having moving part configured to move with the puncture needle, and a sensor provided at a probe body and configured to detect a position of the moving part.

According to a further aspect of the present invention, there is provided a puncture adaptor including a fixed part configured to be fixed at an ultrasonic probe, a moving part movable with the puncture needle toward the ultrasonic probe when the moving part is fixed at the ultrasonic probe, and a sensor provided at probe body and configured to detect a position of the moving part.

According to yet another aspect of the present invention, there is provided a method for detecting an angle of a puncture needle, including detecting a position of a moving part which moves with a puncture needle toward a ultrasonic probe, by a sensor provided at the ultrasonic probe, and detecting information relating to position of the puncture needle on the basis of a detection result of the sensor.

BRIEF DESCRIPTION OF THE SEVERAL VIEWS OF THE DRAWING

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
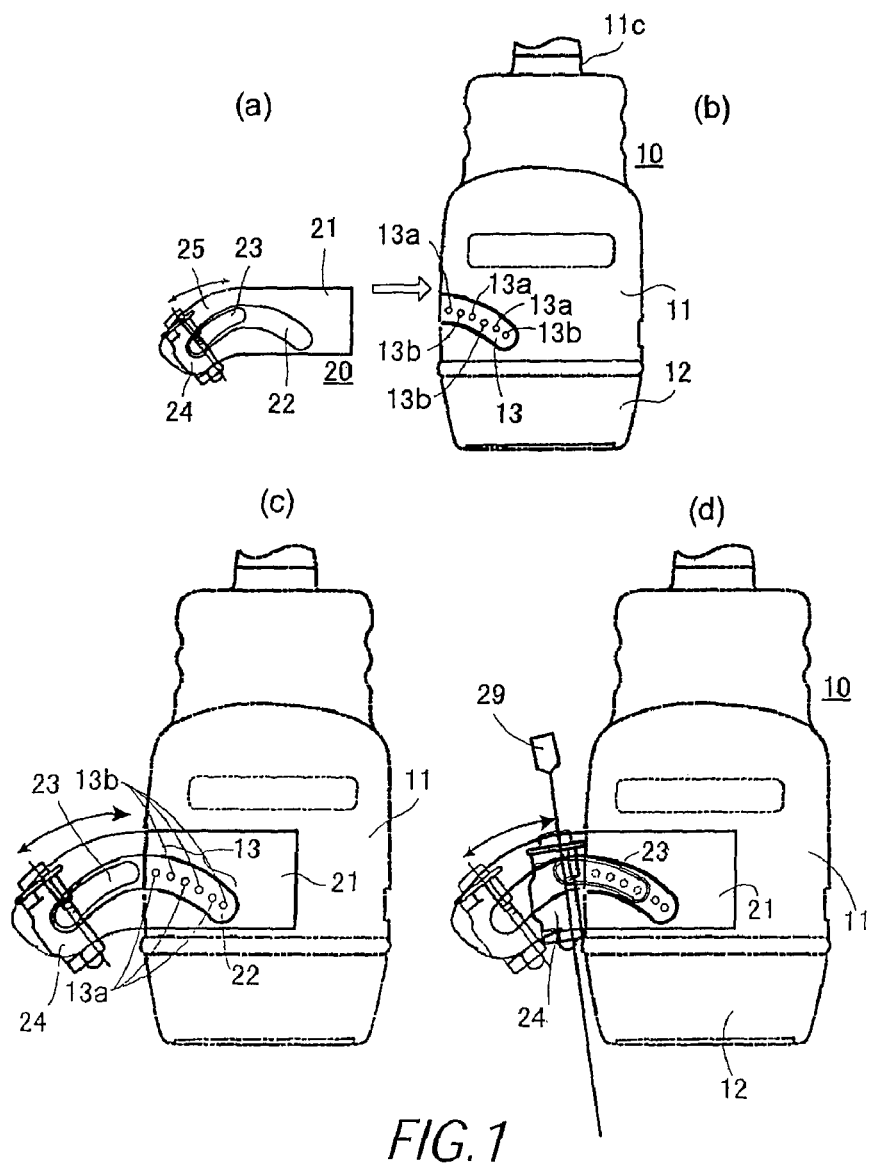
FIGS. 1(a), 1(b), 1(c) and 1(d) are related aspect views of a first exemplary embodiment of the ultrasonic probe and puncture adaptor of the invention.

Referring now to the drawings, wherein like reference numerals designate identical or corresponding parts throughout the several views, various embodiments of the present invention are next described.

First Exemplary Embodiment

An ultrasonic probe 10 shown in FIG. 1 (b) includes a probe body 11 holding an ultrasonic transmit and receiving unit 12 having arrayed ultrasonic transducers, and an alternating photo sensor 13 including luminous elements 13a and light sensitive elements 13b. Lead wires of the luminous elements 13a and the light sensitive elements 13b are wired in a probe body 11. The wires are connected to a body of the ultrasonic diagnostic apparatus through a probe cable 11c with read wires of ultrasonic transducers.

As a slide opening part 22 of puncture adaptor 20 shown in FIG. 1 (a) is positioned opposite the photo sensor 13 of the probe body 11, a holder 21 of the puncture adaptor 20 holds the probe body 11, as shown in FIG. 1(c). A slider 23, having a reflective face facing the probe body 11, is fitted into a slide opening part 22 of the puncture adaptor 20, and a needle guide 24 is fastened at one end of the slider 23 by screws (not shown) to the slider 23 and an adaptor part 25. A puncture needle 29 can be inserted into a puncture needle hole of the needle guide 24 as shown in FIG. 1 (c).

Next, the ultrasonic diagnostic apparatus to which the puncture adaptor 20 attaches, in this exemplary embodiment, is explained with reference to the schematic block diagram of FIG. 2.

Figure 2:
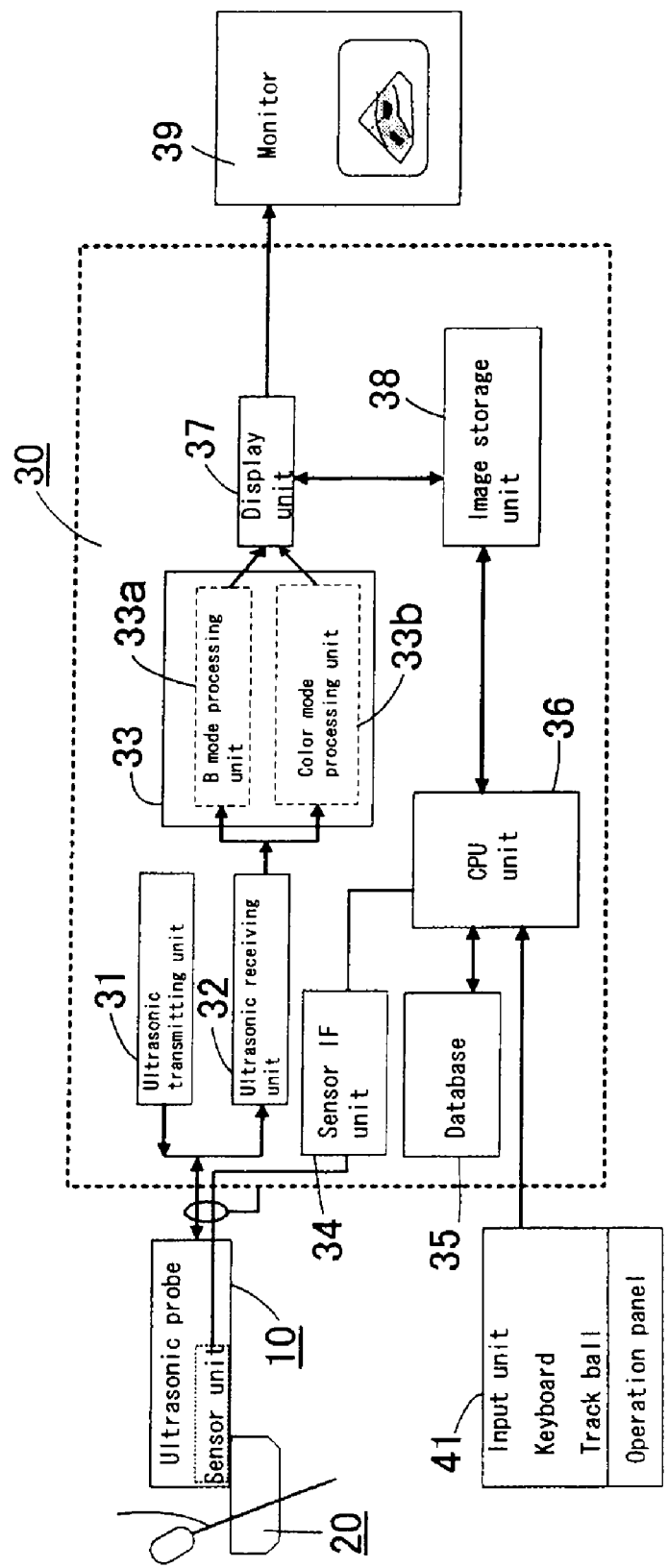
FIG. 2 is a schematic block diagram of a first exemplary embodiment of the invention.

As shown in the FIG. 2, the ultrasonic diagnostic apparatus includes a body 30 connected to an ultrasonic probe 10 with a puncture adaptor 20, an angle sensor signal from the ultrasonic probe 10 is input into the body 30, for processing within the body 30. Also connected to the body 30 is an input unit 41 for user interface with the body 30. The input unit 41 can be a key board, a track ball and/or an operation panel. A monitor 39 for displaying an image signal delivered from the body 30 is also connected to the body 30.

The body 30 includes an ultrasonic transmitting unit 31, an ultrasonic receiving unit 32, an image processing unit 33, a sensor IF (interface) unit 34, a database 35, a CPU unit 36 and a display unit 37. The ultrasonic transmitting unit 31 generates and applies a driving signal to the ultrasonic probe 10. The ultrasonic receiving unit 32 receives a received signal from the probe 10. The image processing unit 33, which includes a B mode processing unit 33a and a color mode processing unit 33b, processes this received signal into an image signal. The sensor IF (interface) unit 34 receives a sensor signal from the ultrasonic probe 10 and converts this signal into an angle signal. The database 35 memorizes and saves a variety of data. The CPU unit 36 controls each of the components of the apparatus on the basis of an operation signal from the input unit 41. The display unit 37 converts a signal from the image processing unit 33 into a display format. An additional image signal like a signal based on a signal from sensor IF 34 is also processed into a graphical signal by this image processing unit 33. The display unit 37 delivers these signals to the monitor 39.

Next, the function and operation of the exemplary embodiment are explained in reference to FIG. 1.

At first, the holder 21 is fixed to the probe body 11 shown in FIG. 1 (b), so that the needle guide 24 of the puncture adaptor 20 lies near the end of the adaptor part 25. Then, as illustrated in FIG. 1(c), all of the luminance elements 13a and the sensitive elements 13b composing the photo sensor 13 are exposed. In this case, each sensitive element 13b which does not receive light emitted from luminance elements 13a likewise does not generate a signal. This position of the needle guide 24 corresponds to a maximum angle of insertion angles (in relation to a vertical insertion angle which is 0 degree) of the puncture needle.

Next, when an operator displaces the needle guide 24 and the slider 23 to the side of the probe body along the slide opening part 22 and reduces the insertion angle of the puncture needle, the slider 23 having a reflective surface on the side facing probe body 11 faces opposite some of the luminance elements 13a and sensitive elements 13b. At that time, light reflected off the reflecting surface impinges on the sensitive elements 13b, and a detection signal is outputted from such sensitive elements 13b. Such detection signals are delivered by a lead wires (not shown in the figures) provided in the probe body 11. These read wires are assembled in the probe cable 11c with read wires for the ultrasonic transducer unit 12 provided at the top of ultrasonic probe 10, and these read wires are connected to the sensor IF unit 34. When the detective signal is inputted to the sensor IF unit 34, the unit measures an angle of the needle guide 24 by detecting how many sensitive elements 13b detect the light from luminance elements 13a. The result of angle detection is delivered to the CPU unit 36.

The CPU unit 36 directs the image storing device 38 to output data of the puncture guide image corresponding to the detected puncture needle insertion angle to the display unit 37. An operator can see the puncture guide image corresponding to a real needle angle on the monitor 39.

In addition, luminous elements 13a and light sensitive elements 13b of the alternating photo sensor 13 are arranged in pairs in the direction of a circular arc in the above explanation. However, pairs of the luminous elements 13a and light sensitive elements 13b may be arranged radially opposite each other with the pairs of luminous element 13a and light sensitive element 13b extending in a circular arc direction. This arrangement enables a high density of sensors and high accuracy of angle detection. In another implementation, the reflecting part of slider 23 may be composed of a plurality of reflecting parts having narrow reed shape, which also enables high accuracy of angle detection.

In the above explanation of the described exemplary embodiment, an ultrasonic diagnostic apparatus reads an angle of the needle guide, and automatically display an insertion position or angle of the puncture needle in an ultrasonic image. This enables provision of an ultrasonic diagnostic apparatus, an ultrasonic probe and a puncture adaptor which avoids a bothersome operation for display of a puncture guide image. In addition, because an angle detection sensor is arranged in the body of the ultrasonic probe, the puncture adaptor has no electrical machinery. Therefore this puncture adaptor can be disinfected and sterilized without concern for breakage or electric leakage caused by body fluids or heat. In addition, because the fabrication cost of the puncture adaptor can be lower than one having sensor, it is possible to treat the adaptor as disposable. Furthermore because read wires for sensor signals are provided in the probe body, it is not necessary that a connecting device be provided outside the probe. Because a cable for the sensor to the diagnostic apparatus body is united with a probe cable for transducers, there is no operability complication caused by an increasing number of cables when the puncture adaptor is used.

Furthermore, in the above explanation of this exemplary embodiment, because it is not necessary that electromagnetic devices be provided on the puncture adaptor, the cost for fabricating the puncture adaptor is lower than the cost for fabricating a puncture adaptor having magnetic elements described in the below mentioned third exemplary embodiment or fourth exemplary embodiment.

Second Exemplary Embodiment

Figure 3:
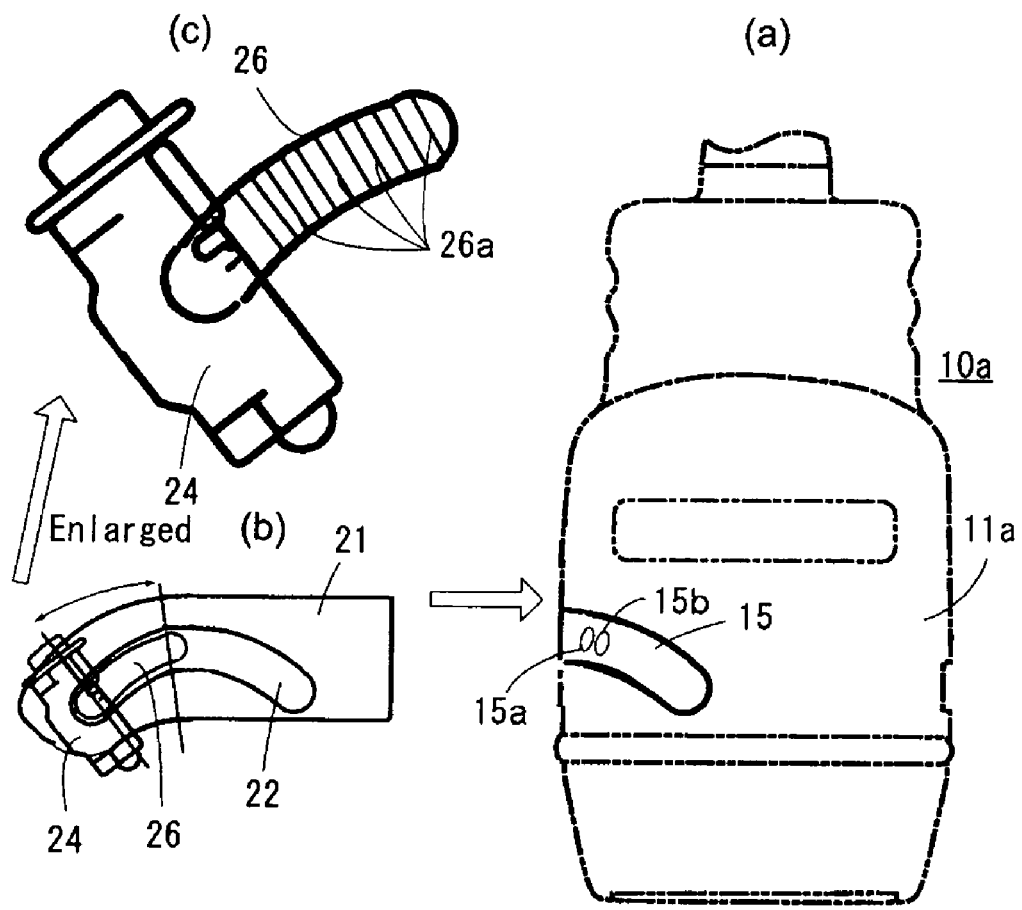
FIGS. 3(a), 3(b) and 3(c) are related aspect views of a second exemplary embodiment of the ultrasonic probe and puncture adaptor of the invention.

In a second embodiment, as shown by FIG. 3, it is characteristic that a pattern having different degrees of reflection, for example a black and white stripe pattern, is provided on a probe body side of the slider 26. The pattern 26a is detected by one pair of a luminance element 15a and a sensitive element 15b provided on the probe body 11. In the explanation of this exemplary embodiment, explanations of similarities with the first exemplary embodiment will be skipped, and differences will be mainly explained.

In this second exemplary embodiment, the needle guide 24 of the puncture adaptor 20 held by the probe body 11a of the ultrasonic probe 10a is moved to a desirable position. By this movement, when the stripe pattern on the slider 26 passes by the luminance element 15a and the sensitive element 15b, the sensitive element 15b receives reflected light from the luminance element intermittently. A read wire for light receiving signals is provided in the probe body 11a and the probe cable, and the signal is delivered to the sensor IF unit 34. This pulse train signal by intermittently receiving light is transformed to angle data by pulse counting of the sensor IF unit 34. The CPU unit 36 directs the image storing device 38 to output data of the puncture guide image corresponding to the detected puncture needle insert angle to the display unit 37. An operator can see the puncture guide image corresponding to an actual needle angle on the monitor 39.

In addition, in order to detect a direction of movement of the puncture needle, the photo sensor 15 may be composed as two sensitive elements and one luminance element between the two sensitive elements. In this case, by detecting each phase of light that enters into two sensitive elements, a direction of movement is distinguished.

Furthermore, the pattern on the slider 26 may be composed as an other monochrome pattern code which indicates puncture angles, for an example bar-code or a QR code (registered trade mark). In this case, the photo sensor 15 reads the code pattern, and the sensor IF unit 34 decodes this code.

In the above explanation of this exemplary embodiment, an ultrasonic diagnostic apparatus reads an angle of the needle guide and displays an insert position or angle of the puncture needle in an ultrasonic image automatically. This enables provision of an ultrasonic diagnostic apparatus, an ultrasonic probe and a puncture adaptor which avoids a bothersome operation for display of a puncture guide image. In addition, because the angle detection sensor is arranged in the body of ultrasonic probe, the puncture adaptor has no electrical machinery. Therefore this puncture adaptor can be disinfected and sterilized without concern for breakage or electric leakage caused by body fluids and heat. In addition, because the fabrication cost of the puncture adaptor can be lower than one having sensor, it is possible to treat the adaptor as disposable. Furthermore because the read wires for sensor signals are provided in the probe body, it is not necessary that connecting devices be provided outside the probe. Because cables for the sensors to the diagnostic apparatus body are united with the probe cable for the transducers, there is no operability complication caused by an increasing number of cables when the puncture adaptor is used.

Furthermore, in the above explanation of this second exemplary embodiment, because it is not necessary that electromagnetic devices be provided on the puncture adaptor, the cost for fabricating the puncture adaptor is lower than the cost for fabricating a puncture adaptor having magnetic elements described in the below mentioned third exemplary embodiment or fourth exemplary embodiment.

In addition, in the above explanation of this second exemplary embodiment, because the number of necessary sensors is two or three, the cost of fabrication of read wires and connecting devices for the sensor can be lower than the case of using more sensors.

Third Exemplary Embodiment

Figure 4:
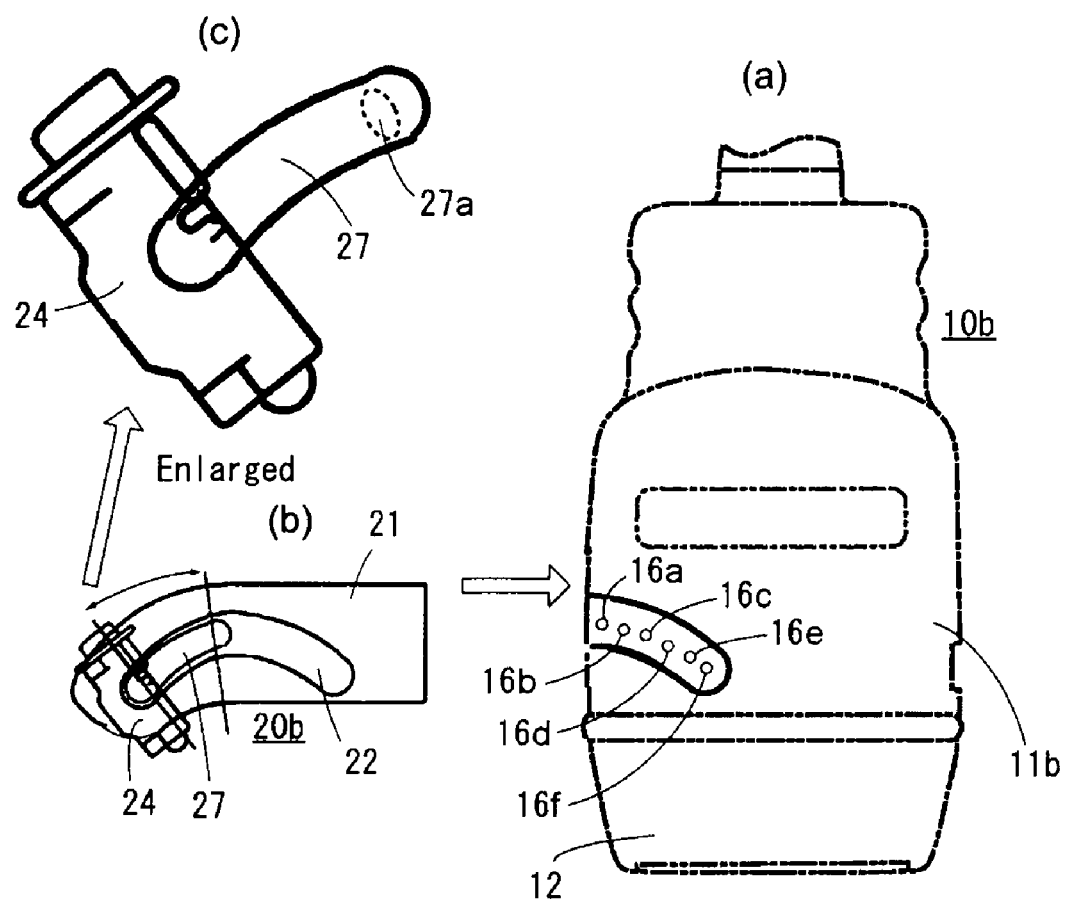
FIGS. 4(a), 4(b) and 4(c) are related aspect views of a third exemplary embodiment of the ultrasonic probe and puncture adaptor of the invention.

In a third exemplary embodiment as shown by FIG. 4, a magnetized magnetic element 27a is provided on the probe body side of the slider 27 and a magnetic sensor unit formed by magneto metric sensors 16a-16f is provided at the probe body 11b in a circular direction. In the explanation of this exemplary embodiment, explanation of similarities with the first exemplary embodiment will be skipped, and differences will be mainly explained.

In this exemplary embodiment, the needle guide 24 of the puncture adaptor 20b held by the probe body 11b of the ultrasonic probe 10b is moved to a desirable position. By this movement, when the magnetic element 27a on the slider 27 passes past the magneto metric sensors 16a-16f, the magnetic metric sensors 16a-16f detect the passing of the magnetic element 27a in turn. A read wire for detecting signals is provided in the probe body 11a and the probe cable, and the signal is delivered to the sensor IF unit 34. When detected signals are inputted to the sensor IF unit 34, the unit 34 measures an angle of the needle guide 24 by detecting how many magneto metric sensors detect the passing. The CPU unit 36 directs the image storing device 38 to output data of the puncture guide image corresponding to the detected puncture needle insertion angle to the display unit 37. An operator can see the puncture guide image corresponding to a real needle angle on the monitor 39.

In the above explanation of this exemplary embodiment, an ultrasonic diagnostic apparatus reads an angle of the needle guide, and displays an insertion position or angle of the puncture needle in an ultrasonic image automatically. This enables provision of an ultrasonic diagnostic apparatus, an ultrasonic probe and a puncture adaptor which avoids a bothersome operation for display of a puncture guide image. In addition, because an angle detection sensor is arranged in the body of the ultrasonic probe, the puncture adaptor has no electrical machinery. Therefore this puncture adaptor can be disinfected and sterilized without concern for breakage or electric leakage caused by body fluid or heat. In addition, because the fabrication cost for the puncture adaptor can be lower than one having sensor, it is possible to treat the adaptor as disposable. Furthermore because read wires for sensor signals are provided in the probe body, it is not necessary that a connecting device be provided outside the probe. Because a cable for the sensor to the diagnostic apparatus body is united with a probe cable for transducers, there is no operability complication caused by an increasing number of cables when the puncture adaptor is used.

Furthermore, in the above explanation of this exemplary embodiment, because of noncontact sensing between the magneto metric sensors and the magnetic element, the magneto metric sensors 16a-16f can be provided inside the case of the probe body 11b. In this case, a surface of the probe body 11b can be formed without irregularities. So a probe washing operation is easy. Because of noncontact sensing, in a case that fluid and tissues of object adhere on the surface of probe body, there is no adverse effect on sensing.

Furthermore, in the above explanation of this exemplary embodiment, it is not necessary that a plurality of magnetic elements be provided on the slider. So the cost for composing puncture adaptor can be lower than the case of below mentioned fourth exemplary embodiment.

Fourth Exemplary Embodiment

Figure 5:
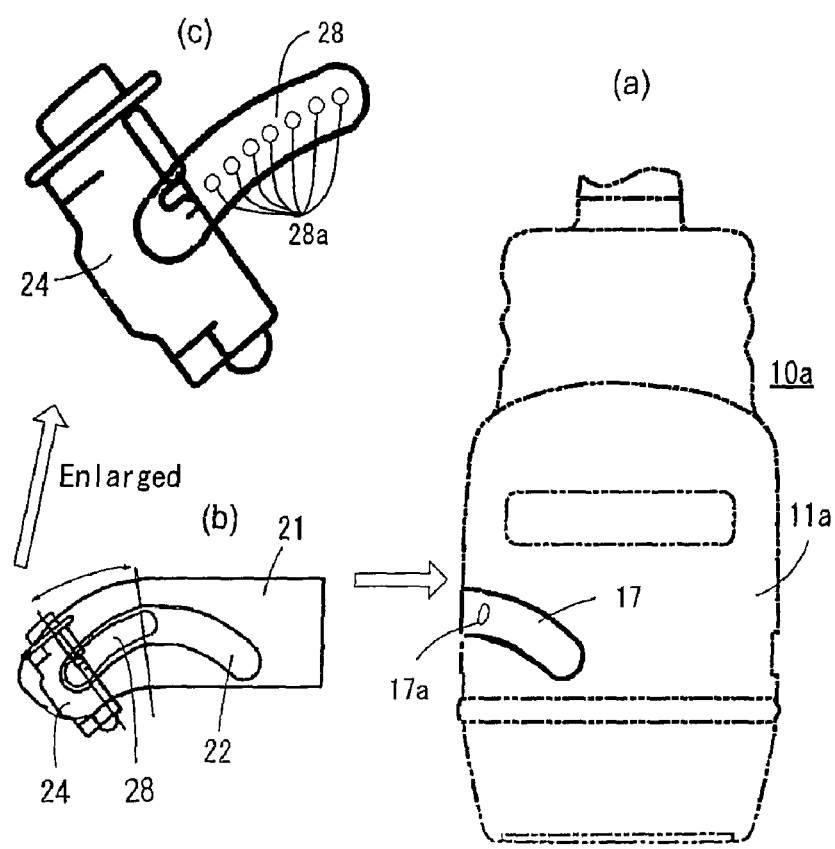
FIGS. 5(a), 5(b) and 5(c) are related aspect views of a fourth exemplary embodiment of the ultrasonic probe and puncture adaptor of the invention.

In a fourth exemplary embodiment, as shown by FIG. 5, plural magnetized magnetic elements 28a are provided on the probe body side of the slider 28 in a circular arc direction. The magnetized magnetic elements 28a are detected by a magneto metric sensor 17a provided on the probe body 11c. In the explanation of this exemplary embodiment, explanation of similarities with the first exemplary embodiment will be skipped, and differences will be mainly explained.

In this exemplary embodiment, the needle guide 24 of the puncture adaptor 20 held by the probe body 11a of the ultrasonic probe 10a is moved to a desirable position. By this movement, when the magnetized magnetic elements 28a on the slider 28 pass adjacent the magneto metric element 17a, the magneto metric element 17a detects passing of the magnetic elements 28a in turn. A read wire for detecting signals is provided in the probe body 11a and the probe cable, and the signal is delivered to the sensor IF unit 34. This pulse train signal produced by intermittent detecting of element 17a is transformed to angle data by pulse counting of the sensor IF unit 34. The CPU unit 36 directs the image storing device 38 to output data of the puncture guide image corresponding to the detected puncture needle insertion angle to the display unit 37. An operator can see the puncture guide image corresponding to a real needle angle on the monitor 39.

In the above explanation of this exemplary embodiment, an ultrasonic diagnostic apparatus reads an angle of the needle guide, and automatically displays an insertion position or angle of the puncture needle in an ultrasonic image. This enables provision of an ultrasonic diagnostic apparatus, an ultrasonic probe and a puncture adaptor which avoids a bothersome operation for display of a puncture guide image. In addition, because an angle detection sensor is arranged in the body of the ultrasonic probe, the puncture adaptor has no electrical machinery. Therefore this puncture adaptor can be disinfected and sterilized without concern for breakage or electric leakage caused by body fluids or heat. In addition, because the fabrication cost of the puncture adaptor can be lower than one having sensor, it is possible to treat the adaptor as disposable. Furthermore because read wires for sensor signals are provided in the probe body, it is not necessary that a connecting device be provided outside the probe. Because a cable for the sensor to the diagnostic apparatus body is united with a probe cable for transducers, there is no operability complication caused by an increasing number of cables when the puncture adaptor is used.

Furthermore, in the above explanation of this exemplary embodiment, because of noncontact sensing between the magneto metric sensor and the magnetic elements, the magneto metric sensor 17a can be provided inside the case of the probe body 11c. In this case, the surface of the probe body 11c can be formed without irregularities. So a probe washing operation is easy. Because of noncontact sensing, in a case that fluid and tissues of object adhere on the surface of the probe body, there is no adverse effect on sensing.

Furthermore, in the above explanation of this fourth exemplary embodiment, it is not necessary that a plurality of magneto metric sensors be provided on the probe body 11c. So the cost of fabricating read wires and connecting devices to the sensor can be lower than the case of using more sensors.

Numerous variations of the present invention are possible in light of the above description. It is therefore to be understood that the invention as claimed can be practiced other than is specifically described herein.

What is claimed is:

1. An ultrasound diagnostic apparatus, comprising:
   an ultrasonic probe configured to transmit and receive ultrasound toward and from a subject;
   a puncture adaptor configured to be fixed directly to the ultrasonic probe, said puncture adaptor including a moving part configured to hold a puncture needle, wherein the moving part is movable toward the ultrasonic probe; and
   a sensor provided within the ultrasonic probe, and configured to detect a position of the moving part when the moving part passes by the sensor.

2. The ultrasonic apparatus according to claim 1, further comprising:
   a read wire provided inside the ultrasonic probe, and configured to deliver a signal from the sensor to outside of the ultrasonic probe.

3. The ultrasonic apparatus according to claim 1, further comprising:
   a displaying unit configured to display information related to a position of the puncture needle based on a signal from the sensor.

4. The ultrasonic apparatus according to claim 1, wherein the sensor comprises:
   a plurality of photo sensors provided along a course of movement of the moving part; and
   a detecting unit configured to detect the position of the moving part based on a state of detection of the photo sensors.

5. The ultrasonic apparatus according to claim 1, wherein:
   the moving part has a reflective pattern so that respective amounts of reflection of at least two different points of the reflective pattern are different from each other; and
   the sensor includes
      a photo sensor provided near a course of movement of the moving part, and
      a detecting unit configured to detect the position of the moving part based on a state of detection of the photo sensor.

6. The ultrasonic apparatus according to claim 1, wherein:
   the moving part includes a magnetic element; and
   the sensor includes
      magneto metric sensors provided along a course of movement of the moving part, and
      a detecting unit configured to detect the position of the moving part based on a state of detection of the magneto metric sensors.

7. The ultrasonic apparatus according to claim 1, wherein:
   the moving part has a magnetic pattern in which at least two different points of the magnetic pattern are different from each other; and
   the sensor includes
      a magneto metric sensor provided near a course of movement of the moving part, and
      a detecting unit configured to detect the position of the moving part based on a state of detection of the magneto metric sensor.

8. The ultrasonic apparatus according to claim 1, wherein:
   the sensor comprises one of an electromagnetic induction sensor, an electro capacitance sensor and an ultrasound sensor.

9. An ultrasonic probe, comprising:

a body;

a puncture adaptor configured to be fixed directly to the body of the ultrasonic probe, said puncture adaptor including a moving part configured to hold a puncture needle, wherein the moving part is movable toward the ultrasonic probe; and a sensor provided within the ultrasonic probe and configured to detect a position of the moving part when the moving part passes by the sensor.

10. The ultrasonic probe according to claim 9, wherein the sensor comprises:

a plurality of photo sensors provided along a course of movement of the moving part; and a detecting unit configured to detect the position of the moving part based on a state of detection of the photo sensors.

11. The ultrasonic probe according to claim 9, wherein:

the moving part has a reflective pattern in which respective amounts of reflection of at least two different points of the pattern are different from each other; and the sensor includes a photo sensor provided near a course of movement of the moving part, and a detecting unit configured to detect the position of the moving part based on a state of detection of the photo sensor.

12. The ultrasonic probe according to claim 9, wherein:

the moving part includes a magnetic element; and the sensor includes magneto metric sensors provided along a course of movement of the moving part, and a detecting unit configured to detect the position of the moving part based on a state of detection of the magneto metric sensors.

13. The ultrasonic probe according to claim 9, wherein:

the moving part has a magnetic pattern in which at least two different points of the magnetic pattern are different from each other; and the sensor includes a magneto metric sensor provided near a course of movement of the moving part, and a detecting unit configured to detect the position of the moving part based on a state of detection of the magneto metric sensor.

14. The ultrasonic probe according to claim 9, wherein:

the sensor comprises one of an electromagnetic induction sensor, an electro capacitance sensor and an ultrasound sensor.

15. A method for detecting an insertion angle of a puncture needle, comprising:

detecting a position of a moving part using a sensor provided within an ultrasonic probe, wherein the moving part moves with the puncture needle toward the ultrasonic probe and passes by the sensor; and generating information relating to a position of the puncture needle based on a detection result of the sensor.

* * * * *